United States Patent [19]

Kazmerski

[11] Patent Number: 4,874,946
[45] Date of Patent: * Oct. 17, 1989

[54] METHOD AND APPARATUS FOR ANALYZING THE INTERNAL CHEMISTRY AND COMPOSITIONAL VARIATIONS OF MATERIALS AND DEVICES

[75] Inventor: Lawrence L. Kazmerski, Lakewood, Colo.

[73] Assignee: The United States of America as represented by the United States Department of Energy, Washington, D.C.

[*] Notice: The portion of the term of this patent subsequent to Nov. 17, 2004 has been disclaimed.

[21] Appl. No.: 728,970

[22] Filed: Apr. 30, 1985

[51] Int. Cl.$^4$ .................. H01J 37/252; G01N 23/225
[52] U.S. Cl. ................................. 250/309; 250/310; 250/307; 250/288
[58] Field of Search ............... 250/309, 310, 307, 306, 250/305, 288

[56] References Cited

U.S. PATENT DOCUMENTS

| | | | |
|---|---|---|---|
| 3,329,813 | 7/1967 | Hashimoto | 250/49.5 |
| 3,840,743 | 10/1974 | Tamura et al. | 250/307 |
| 3,881,108 | 4/1975 | Kondo et al. | 250/307 |
| 3,889,115 | 6/1975 | Tamura et al. | 250/307 |
| 3,909,612 | 9/1975 | Gibbard | 250/307 |
| 3,916,190 | 10/1975 | Valentine et al. | 250/305 |
| 3,916,191 | 10/1975 | Leys et al. | 250/306 |
| 3,986,025 | 10/1976 | Fujiwara et al. | 250/306 |
| 4,236,073 | 11/1980 | Martin | 250/309 |
| 4,476,386 | 10/1984 | Reid et al. | 250/310 |

Primary Examiner—Bruce C. Anderson
Assistant Examiner—Jack I. Berman
Attorney, Agent, or Firm—Kenneth L. Richardson; John M. Albrecht; Judson R. Hightower

[57] ABSTRACT

A method and apparatus is disclosed for obtaining and mapping chemical compositional data for solid devices. It includes a SIMS mass analyzer or similar system capable of being rastered over a surface of the solid to sample the material at a pattern of selected points, as the surface is being eroded away by sputtering or a similar process. The data for each point sampled in a volume of the solid is digitally processed and indexed by element or molecule type, exact spacial location within the volume, and the concentration levels of the detected element or molecule types. This data can then be recalled and displayed for any desired planar view in the volume.

19 Claims, 4 Drawing Sheets

METHOD AND APPARATUS FOR ANALYZING THE INTERNAL CHEMISTRY AND COMPOSITIONAL VARIATIONS OF MATERIALS AND DEVICES

CONTRACTUAL ORIGIN OF THE INVENTION

The United States Government has rights in this invention under Contract German Pat. No. C02-83CH10093 between the U.S. Department of Energy and the Solar Energy Research Institute, a Division of Midwest Research Institute.

BACKGROUND OF THE INVENTION

1. Field of the Invention

This invention relates generally to compositional analysis techniques of materials and devices, and more specifically to a method and apparatus for analyzing the chemical composition and physical distribution of molecular substances in solid materials, such as semiconductors and similar devices.

2. Description of the Prior Art

It is well-known and generally accepted that single crystal materials, such as silicon, indium, copper, selenium, and others make the most effective and efficient semiconductor materials for use as solar cells and other electronic devices. It is also known and generally understood that the time and meticulous controls necessary for growing such single crystalline materials make them uneconomical for large-scale or mass produced uses, at least under present technological limitations in this field. As a result, more attention has been directed recently toward less perfect, but more easily and less expensively produced materials, such as polycrystalline and amorphous silicon and other similar materials for use as solar cells and other semiconductor devices.

Polycrystalline materials, while easier and less expensive to produce than single crystal materials, generally do not make as good or efficient semiconductor devices as single crystal materials. The crystalline grain boundaries or other defects in polycrystalline materials adversely affect the performance of these materials as semiconductors, and particularly as effective photovoltaic converters or solar cells.

Both the understanding and control of the behavior of grain boundaries, particularly in polycrystalline silicon (Si), have advanced substantially in recent years. As a result, the adverse effects of the grain boundaries on the performance of polycrystalline Si semiconductors is now attributed to essentially four mechanisms. First, these intercrystalline boundaries can impede the flow of majority charge carriers, increasing the series resistance of the device. Second, dangling or unfilled bonds at the grain boundaries can provide electrical shunts across the polycrystalline layer, thereby reducing both the fill-factor and the open-circuit voltage. Third, impurities in the grain boundaries can act as recombination centers across the forbidden band gap for the minority carriers, thus decreasing the electric field across the junction. Fourth, these grain boundaries can serve as enhanced diffusion paths for impurity species into the semiconductor device, which can react and degrade the chemical structure of the material, thus limiting and decreasing the operational lifetime of the solar cell.

Efforts are now being made to develop methods and techniques for minimizing or eliminating these adverse effects of grain boundaries in crystalline semiconductor and solar cell materials. For example, techniques have been developed to segregate oxygen and other impurities to the grain boundaries by heat treatments or high-temperature processing and then passivating these grain boundaries by incorporation of hydrogen therein to form silicon hydroxide (SiOH) molecules, which have completely satisfied bonds, thus reducing the deleterious effects of dangling bonds at the grain boundaries.

This technique and others show promise of improving the performance of polycrystalline solar cells and semiconductor devices. However, prior to this invention, there was no effective technique available for obtaining data and analyzing the precise chemical and compositional makeup of the grain boundaries including the impurity distribution in the grain boundaries. Thus, it has been very difficult, and largely an educated guessing process, to determine the chemical substances present in the grain boundaries and the effectiveness of various correctional techniques.

Attempts have been made to fracture polycrystalline materials along grain boundaries to expose these interfaces to direct chemical analysis. However, this technique has several serious problems. First, it is very difficult to fracture the material precisely where analysis is desired. For example, after gaining experience, about one out of 60 fractures of a polycrystalline silicon sample is successful at exposing the desired region. Even then, a successful fracture exposes only part of the grain boundary. The other part is lost, usually to the bottom of the analysis chamber. Thus, there is a high probability that the real information of interest to the problem may be lost. Further, multiple or subsequent processing (e.g., diffusion or heat treatment) cannot be accomplished on a given sample segment since the fracture procedure is violently destructive.

Other techniques have included the use of conventional surface analysis methods, such as Auger electron spectroscopy (AES), secondary ion mass spectroscopy (SIMS), or X-ray photoelectron spectroscopy (XPS) in conjunction with sputter etching. These conventional techniques are focused on a point on the material's surface and are adapted to detect the chemical makeup of the material on that point. Therefore, when combined with sputter etching of the surface to provide depth, the point of analysis becomes a line analysis. Such techniques provide compositional information about the elements and molecular species along a line perpendicular to the surface. However, if the intent is to observe and resolve the composition of a plane (e.g., the map of impurities that may have segregated to some internal grain boundary or surface), these conventional profiling techniques cannot be utilized. They would give information only on a small region or point on the internal surface or grain boundary, provided the analyst is fortunate enough to take the data while passing through the internal surface or grain boundary during analysis. Further, while grain boundaries are very thin and appear as surfaces, they are actually three-dimensional regions where impurities can concentrate, so it is really not possible to observe the actual chemical and compositional make up of a grain boundary region from the point or even line data obtainable with conventional AES, SIMS, or XPS analysis techniques, even when they are performed in conjunction with sputter etching.

SUMMARY OF THE INVENTION

Accordingly, it is a general object of the present invention to provide a method and apparatus for obtaining a direct and complete analysis of the internal chemistry and compositional variations of materials and devices.

It is a specific object of this invention to provide a method and apparatus for obtaining data from a three-dimensional microvolume of a solid semiconductor device relating to element or molecular species, the concentration of that particular element or molecular species, and the exact location of the detected species in the microvolume.

Still another object of the present invention is to provide a method and apparatus for mapping and indexing elements and molecular species in a volume by spatial location, type, and concentration.

A still further object of the present invention is to provide a method and apparatus for recalling and displaying for observation and analysis the element or molecular type of material present and the concentration thereof on the surface of any desired plane in the microvolume of material tested and mapped.

Additional objects, advantages, and novel features of this invention are set forth in part in the description that follows, and in part will become apparent to those skilled in the art upon examination of the following specification, or may be learned by the practice of the invention. The objects and advantages of the invention may be realized and attained by means of the instrumentalities and in combinations pointed out in the appended claims.

To achieve the foregoing and other objects in accordance with the purpose of the present invention, as embodied and broadly described herein, the method of this invention may comprise the steps of gradually removing a selected volume of a solid device and during such removal, sampling and determining the chemical type and concentration of materials from various points in the volume, and displaying the types and concentrations of such materials from points in a selected plane. The points are selected and sampled by rastering a point source analyzer over the exposed surface of the column as the materials are being removed by a process such as sputtering, which is capable of removing the materials in separate molecular form. The chemical types and concentrations of the materials are determined by methods of SIMS, AES, or XPS. The information for each sampling point, including location, (preferably on an X, Y, Z, coordinate system) chemical type, and concentration are recorded by a computer in a data base for recall and display by the sampled points in a selected plane in the volume. The preferred planar display uses individual colors representing each type of material.

To also achieve the foregoing and other objects in accordance with the purpose of the present invention as well as to facilitate the practice of the method of this invention, the apparatus of this invention may comprise a material erosion or removal device (such as a vacuum sputtering system for eroding the solid device, a device) for analyzing or determining the chemical or molecular identities of the material being removed at selected points on the surface of the eroding area (such as a SIMS, AES, or XPS area (such modified to focus on a series of selected points automatically), a recording and storage device (such as a computer for recording and storing for later recall the types and concentrations of chemicals or molecules eroded from the selected points) and a display device, (such as a plotter or video CRT for displaying the types and concentrations of chemicals or molecules detected from selected combinations of the points; for example, the points in a selected plane in the volume).

BRIEF DESCRIPTION OF THE DRAWINGS

The accompanying drawings, which are incorporated in, and form a part of, the specifications, illustrate the preferred embodiments of the present invention and together with the description, serve to explain the principles of the invention. In the drawings.

DETAILED DESCRIPTION OF THE PREFERRED EMBODIMENT

Figure 1:
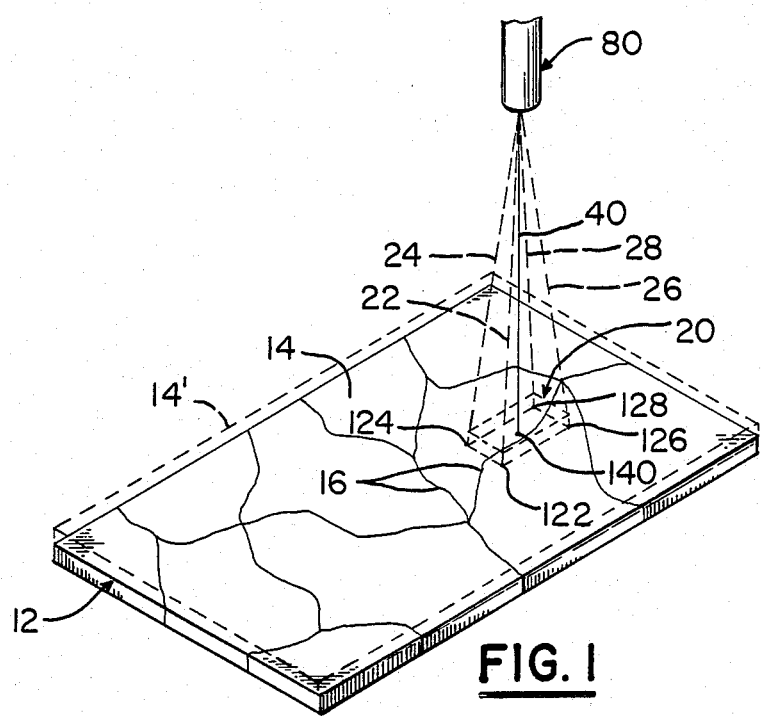
FIG. 1 is an isometric view of a partially eroded solid, polycrystalline device and a mass analyzer device positioned over the eroding surface of the polycrystalline device for detecting the chemical types and concentrations of ions being eroded from various selected points within a selected microvolume of the polycrystalline device.

The present invention includes a method and apparatus for analyzing, recording, and displaying the chemical composition of a microvolume 20 of a solid device, such as the polycrystalline silicon wafer 12 illustrated in FIG. 1. Actually, only a portion of the original polycrystalline wafer 12 shown in FIG. 1 remains. The outline of its original volume is illustrated by the broken lines 14'. Part of the method of this invention includes the step of etching or eroding away the wafer 12 while detection and analysis of the microvolume 20 proceeds, as will be described in more detail. Such etching or erosion is preferably accomplished by a vacuum sputtering process, although there are a variety of other known procedures that could be used to remove layers of the silicon wafer material to anlayze the chemical composition of its interior. Therefore, the wafer 12 and mass analyzer apparatus 80 are assumed to be positioned for purposes of this description in a vacuum sputtering chamber, which is not shown in the drawings since such vacuum sputtering chambers are conventional and well-known to persons skilled in this art, and such persons will readily understand the operation and function of such sputtering in this description.

Figure 2:
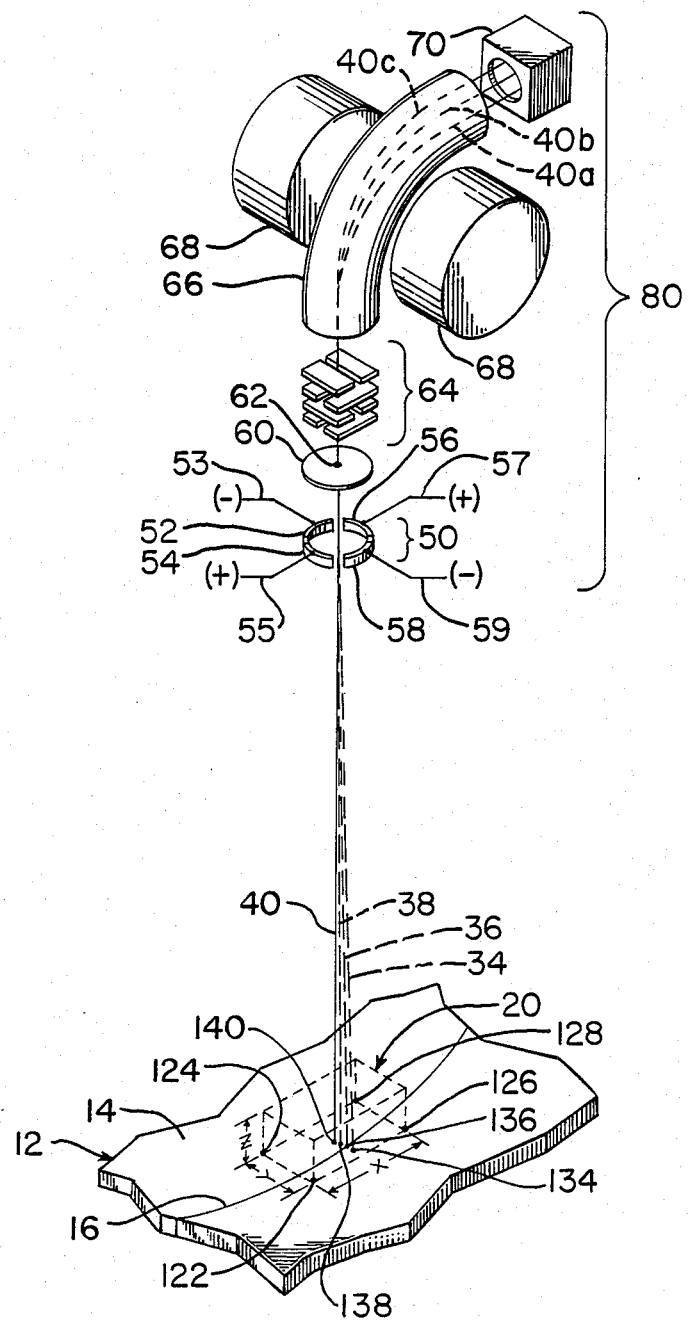
FIG. 2 is an enlarged isometric schematic view of the microvolume of the eroding polycrystalline device from which the chemical composition is being analyzed, including an isometric schematic view of the principle operating features of a SIMS mass analyzer necessary to describe this invention.

Also, the preferred embodiment of this invention utilizes a SIMS system, as shown in FIGS. 1 and 2, for detecting and analyzing the chemical composition of the microvolume 20. Other analyzer systems, such as an AES or XPS, can also be used to determine the chemical composition of the microvolume 20. SIMS is preferred for analysis of grain boundaries in polycrystalline silicon devices, such as that illustrated and described herein, because SIMS has a high sensitivity to trace elements and is unique in its ability to detect hydrogen, an element that shows promise as an agent in grain boundary passivation. Therefore, this description will include only so much of a fundamental description of a SIMS system as is necessary to describe this invention, and persons skilled in this art will undoubtedly then recognize the application of other analyzers such as AES and XPS systems without further explanation herein. In this regard, the illustration of a SIMS system in FIG. 2 and the associated description herein is only schematic and is not intended as a complete description of state-of-the-art SIMS systems.

It should also be noted that dimensions of the microvolume 20 and the increments of movement of the analyzing technique to be described herein are extremely small and are measured in terms of microns and angstroms (Å). Therefore, the illustrations in the accompanying drawings are of necessity exaggerated in size and are not shown in actual proportions. However, they do illustrate the principal features and functions of this invention.

Referring again to FIG. 1, the vacuum sputtering process creates a plasma of the components on the surface 14 of the polycrystalline silicon wafer 12 as the sputtering process erodes away the surface 14. The plasma is typically a very high-temperature, gaseous mixture of segregated molecules and ions of the wafer material eroded from the surface 14 by electron bombardment in an evacuated space confined by a magnetic field (not shown). The SIMS 80 is capable of receiving a sample of ions eroded from any of a plurality of selected points on the surface 14 of the wafer 12 and detecting or analyzing the chemical composition of the material being eroded from the point, as will be described in more detail.

A significant feature of this invention is the ability to systematically collect chemical composition data from many points on the eroding surface 14. As the surface erodes, additional points are sampled and chemical composition data are collected from such points so that such data are obtained from many points throughout a defined microvolume 20 of the wafer 12. In the illustration in FIG. 1, the selected microvolume 20 to be scanned and analyzed includes a grain boundary 16, where the chemical composition is of particular interest to an analyst, and which provides a basis for demonstrating the capabilities of this invention.

The SIMS 80 is shown receiving a beam of ions 40 originating from point 140 on the surface 14 in the microvolume 20. The outer extremities of the selected microvolume 20 are defined by the corner points 122, 124, 126, 128 as sampled by the SIMS 80 in ion beam paths illustrated respectively by broken lines 22, 24, 26, 28 to represent ion beam paths where samples are not being taken at the instant of this illustration. The ion beam path 140, on the other hand, is represented in a solid line to indicate that the sample is presently being taken and analyzed from point 140 at the instant of this illustration. This convention will be followed throughout this description for purposes of clarity.

This system is shown enlarged and in more detail in FIG. 2, wherein only a broken away segment of wafer 12 is shown because of to space limitations in the drawing. Also, the basic operational components are illustrated in an exploded schematic in FIG. 2. To describe this invention with greater clarity, a brief description of the SIMS 80 is provided.

An ion beam 40 originating from the sputtering plasma at a point 40 on the surface 14 of the eroding wafer 12 is directed through an inlet aperture 62 in a plate 60 at the entrance of the SIMS 80. The ion beam 40 is then directed through a plurality of acceleration and focusing slots 64, which accelerate the ion beam 40 into the mass segregation tube 66. A strong magnetic field perpendicular to the ion beam 40 is generated by a magnetic source 68. This magnetic field diverts the ion beam into a curved path through the segregation tube 12. The mass of the respective ions determines the extent to which the respective ions are diverted from a straight to a curved path. The mass of each ion is indicative of its chemical structure.

In the simplified illustration of FIG. 2, the ion beam 40 originating from point 140 is shown segregated into three mass groups or beams 40a, 40b, 40c, representing three major chemical constituents. In real operations, there can and usually will be more than three chemical constituents, thus more than three segregated beams in the segregation tube 66. However, the three beam groupings 40a, 40b, 40c, described herein are sufficient to illustrate this invention, and they can correspond conveniently to the three major chemical compositions of silicon (Si), silicon oxide (SiO), and silicon hydroxide (SiOH) normally found and studied in grain boundaries of polycrystalline silicon wafers that have been subjected to hydrogen passivation techniques, as will be described in more detail.

The segregated ion mass beams are then directed into a mass detector or analyzer 70 where the actual masses, thus chemical structures, of the beam components are determined. These data are then sorted and fed into a computer for storage and recall, as will be described in more detail below.

The particular points on the surface 14 from which ions are sampled and analyzed by the SIMS 80 are controlled by the raster control assembly 50. This raster control assembly 50 is comprised of a ring divided into a plurality of electronically separated segments such as the four segments 52, 54, 56, and 58 illustrated in FIG. 2. Some of these segments, such as 52, and 58, are negatively charged, and some, such as segments 54, and 56, are positively charged. Therefore, by selecting ions (usually cations because they are generally significantly more abundant) for analysis, the origination points for such ions can be precisely determined and controlled by varying the relative positive and negative voltages on the respective ring segments 52, 54, 56, and 58. At the same time, substantially all ions and molecules not originating from the selected point are diverted away from the inlet aperture 62. Thus, the chemical composition being detected or analyzed by the SIMS 80 at any one time can be precisely limited to those chemical constituents originating at a selected point on the surface 14 of the eroding wafer 12. This structure 50 is referred to as an electrostatic lens.

For example, as shown in FIG. 2, an ion beam 40 originating from point 140 on the sputtering surface 14 is being directed into the SIMS 80 for mass analysis to determine the chemical composition of the material at point 140. A slight change in voltage in the ring segments 52, 54, 56, and 58 can cause an ion beam 38 from point 138 to be directed into the SIMS 80. Additional voltage changes can cause ion beams from other points, such as ion beam 36 from point 136 or ion beam 34 from point 134, to be directed into the SIMS 80. Thus, the electrostatic lens 50 can be controlled by varying the voltages therein to raster the point origins of ion beams over a selected surface area to gather chemical composition data from each of such points. The increments of distance between such points has been found to be fairly linear in relation to voltage changes required to shift the points in such increments over distances up to approximately 40 microns; however, actual calibration is recommended.

Figure 3:
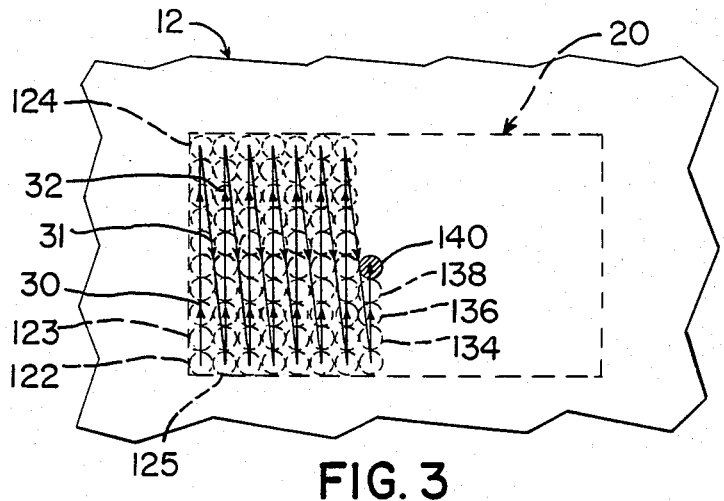
FIG. 3 is an enlarged plan view of the microvolume being analyzed, and showing schematically a rastering pattern used by the invention in the SIMS mass analysis process.

For the purposes of this invention, a raster pattern such as that illustrated in FIG. 3 is effective, although other raster patterns can certainly be used to accomplish the same results. In FIG. 3, the electrostatic lens 50 is first focused to direct ions from position or dot 122 into the SIMS 80. After a sufficient increment of time to allow a SIMS mass analysis of the chemical components originating from that point, the voltage is changed in the electrostatic lens 50 to direct ions from an adjacent point 123 into the SIMS 80. This raster pattern proceeds to successive points along the path indicated by arrow 30 to the corner point 124. From there, the raster shifts over one column and back to point 125 adjacent the starting point 122, as indicated by arrow 31. This pattern then continues as indicated by arrow 32 to repeat itself over the selected surface area, as shown in FIG. 3. The present point 140 being analyzed by this SIMS 80 and the three immediately preceding points 134, 136, 138, as shown in FIG. 2 and discussed above, are also illustrated in FIG. 3.

The outer extremities of the raster pattern define the surface area of the microvolume 20 being analyzed. Raster increments of about 5,000Å to 8,000Å are effective in illustrating the chemical composition of the microvolume 20. A surface area of about 40 microns by 25 microns is an effective analysis tool for polycrystalline silicon wafers.

The chemical compositional data from each point is analyzed and stored in a computer data base, along with the location of the point from which such data was taken. The location of each point is preferably recorded in the format of an X, Y, Z coordinate system so it can be recalled and displayed conveniently, along with its corresponding chemical composition information, if desired.

The X and Y location for each point can be determined conveniently by keeping track of the raster increments from a starting or reference point, as described earlier. The Z or depth coordinate location is preferably determined by multiplying a known sputtering erosion rate by the time between the beginning of the sputtering and that point when the respective sample is taken. Sputtering rates for such common materials as silicon are usually known or can be determined for specific sputtering apparatus or procedures. For example, one can simply measure the depth of the crater or material sputtered away and divide by the time it took to sputter to that depth. For common substances such as silicon, the rate of erosion is known and the Z dimension can be determined within 20Å. Timing the raster increments to cover the selected surface for each 200Å to 500Å of erosion depth provides satisfactory results.

Thus, a predetermined surface area on the surface of the wafer 12 is selected for the SIMS analysis. The electrostatic lens 50 is focused on a starting point, and the sputtering is begun at a set rate. As ions are eroded from the surface 14, the SIMS determines the chemical composition of the ions being eroded at the starting point. Then, at predetermined time increments, the voltage is varied on the electrostatic lens 50 to raster the SIMS analysis points over the entire preselected surface area, as illustrated in FIG. 3.

When the entire preselected surface area, usually about 40 microns by 25 microns, has been rastered and the chemical composition data taken from each raster point, the electrostatic lens is reset again to the original starting position to raster the surface area again. However, by that time additional material will have been eroded by the sputtering so that the second rastered area is about 200Å to 500Å deeper into the wafer, depending on the sputtering rate and raster timing selected. Thus, the data collected from the second repeated raster pattern will be from points about 200Å to 500Å farther into the wafer 12 than the first pattern. As these raster patterns are repeated while the wafer 12 continues to be sputtered away, the collected data are from a pattern of points defining a solid portion or microvolume 20 of the original wafer 12.

Figure 7:
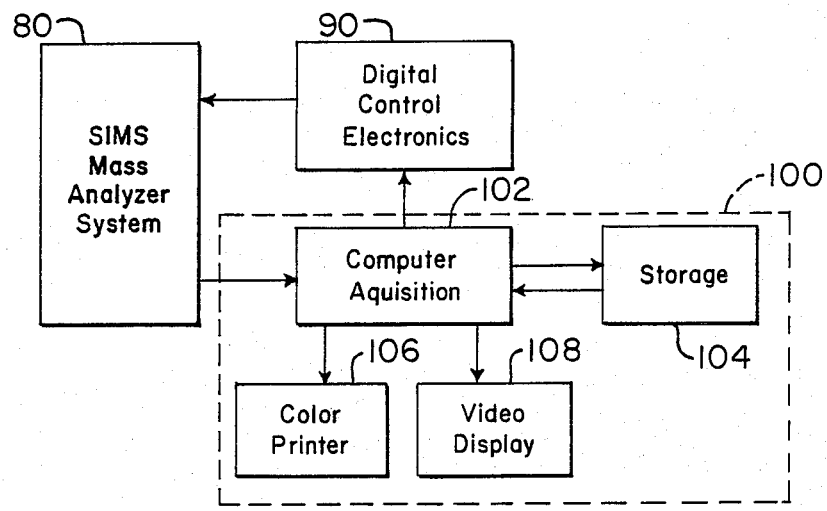
FIG. 7 is a block diagram of the interrelationship of the several components of this invention.

Referring now to FIG. 7, a computer 100 can be utilized conveniently to control the raster process, as well as to receive, store, and recall for display the data determined or detected for each point. More specifically, the computer 100 activates digital control electronics 90 to raster the SIMS 80 over the surface of the device to be analyzed in the increments of distance and time selected by the user. The computer acquisition system 102 also acquires the mass analysis data from the SIMS 80 and stores the data in computer storage 104, such as a hard disk system. Such data can be recalled by the computer acquisition system 102 and displayed, for example, on a color printer or plotter 106 or on a video display screen 108.

Figure 8:
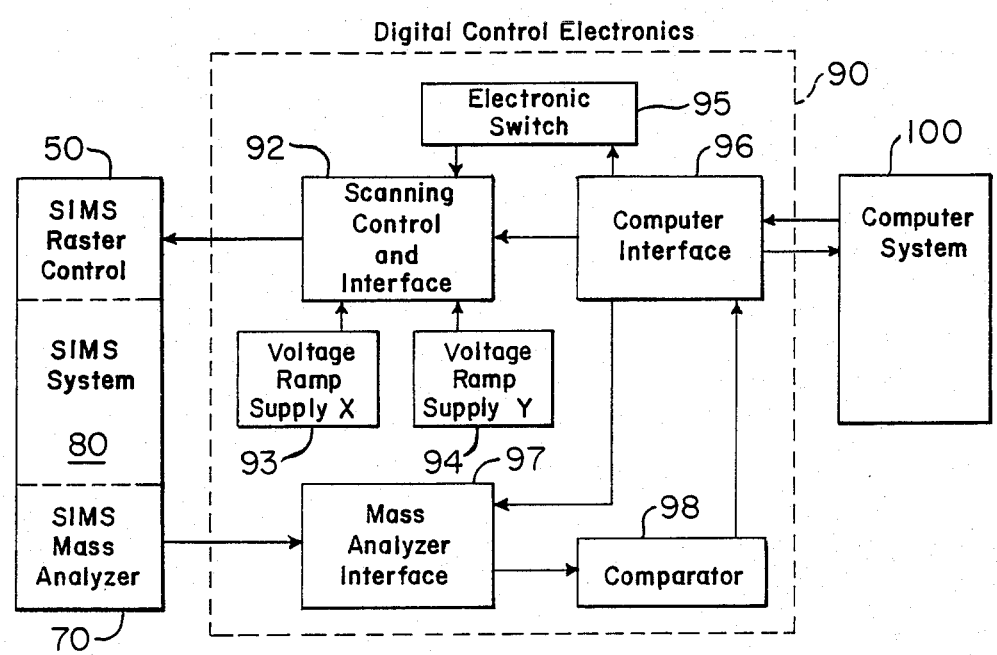
FIG. 8 is a block diagram of the digital control electronics shown in FIG. 7.

The digital control electronics 90 is illustrated in more detail in FIG. 8. A computer interface 96 is provided to convert data into a format that can be accepted and used by the computer 100 and to convert information output from the computer into electronic formats usable by the various computer-controlled components. Actual electonic circuits for these components can be designed in several ways that are readily apparent to persons skilled in the art. Thus, it is not necessary to describe or illustrate such actual circuits for the purpose of describing this invention.

The scanning control and interface receives signals from the computer 100 through the computer interface 96 that are provided to drive the raster control or electrostatic lens 50 of the SIMS 80. For example, the computer 100 is programmed to control the size of the area to be scanned by the SIMS 80, the raster increments of both space and time between each point, and the raster patterns. The scanning control and interface 92 converts these control signals from the computer into changes of voltage applied to the electrostatic lens 50 to actually change the points from which ions are received by the SIMS 80 for analysis, as described earlier. To facilitate this operation, voltage ramp supplies 93, 94 are provided and connected to the scanning control and interface 92 as voltage sources for moving the scanned point in the X and Y directions, respectively.

An electronic switch 95 is provided to activate and deactivate the scanning control and interface 92 upon command signals from the computer 100. When the electronic switch 95 activates the scanning control and interface, the SIMS 80 can function in the raster mode described earlier according to this invention. When it is deactivated, the SIMS 80 is fixed and can operate only in the conventional manner receiving ions from only one point for analysis.

A mass analyzer interface 97 is also connected to the computer interface 96. This mass analyzer interface receives the electronic output from the SIMS ion mass analyzer 70 and converts such output into signals that can be utilized by the computer 100 corresponding to the ion masses, i.e., chemical identities of the ions, originating from the points on the solid surfaces being analyzed. A comparator 98 is provided to identify the mass/chemical identity relationship of the SIMS mass analyzer 97 output, and such output can be screened or filtered to allow recording of only selected kinds, groups, or concentrations of ions detected.

For example, for simplicity, as described above, the ion beam 40 in FIG. 2 is shown divided into three distinct mass beams 40a, 40b, and 40c. In reality, it is likely that additional impurities or substances in the wafer 12 will result in segregation of more than just the three separate mass beams 40a, 40b, 40c, illustrated in FIG. 2. However, each ion type requires over 5 megabytes of computer storage to process. Thus, it may be desirable to limit analysis to only three or four ion or chemical types, depending on computer storage capacity available.

For purposes of further explanation of the functions and benefits of this invention, reference is made to the background section of this specification wherein the mechanisms of grain boundaries contributing to adverse effects on the performance of polycrystalline silicon semi-conductors are discussed. The presence of oxygen at the grain boundaries 16 is largely responsible for many of the deleterious effects. Such oxygen is usually found in the form of SiO molecules, which have the dangling bonds that reduce the fill-factor and open-circuit voltage of the device. As noted in the background, introduction by hydrogen into the grain boundaries to combine with the SiO to form SiOH has the beneficial effect of filling, thus eliminating dangling bonds in the grain boundary. Many experiments are being conducted to find effective methods of getting hydrogen into the grain boundaries. Thus, it would be useful to be able to determine whether such hydrogen penetration into the grain boundaries is being accomplished effectively. The present invention can facilitate such analysis.

For example, if one wanted to know whether hydrogen passivation of grain boundaries in a polycrystalline silicon wafer 12 was effective and the extent to which hydrogen penetrated the grain boundaries in such a process, the wafer caned be positioned as shown in FIGS. 1 and 2 such that the selected SIMS analysis microvolume 20 included a segment of the grain boundary 16. The comparator 98 and computer system 100 can be set to record the presence and concentrations of Si, SiO, and SiOH detected by the SIMS mass analyzer 70 for each point sampled in the microvolume 20. Thus, as the wafer 12 is sputtered away, and the SIMS electrostatic lens 50 is rastered through the microvolume 20, the Si, SiO, and SiOH present at each point is detected by the SIMS mass analyzer 70 and recorded in the computer storage along with the X, Y, and Z coordinates of the location of each point in the microvolume 20.

Figure 5:
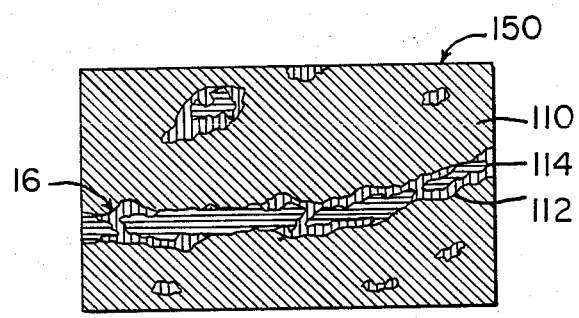
FIG. 5 is an example of a two-dimensional plan view of the chemical compositional display of the grain boundary in a plane therethrough being viewed from the aspect of arrow A shown in FIG. 4.
Figure 6:
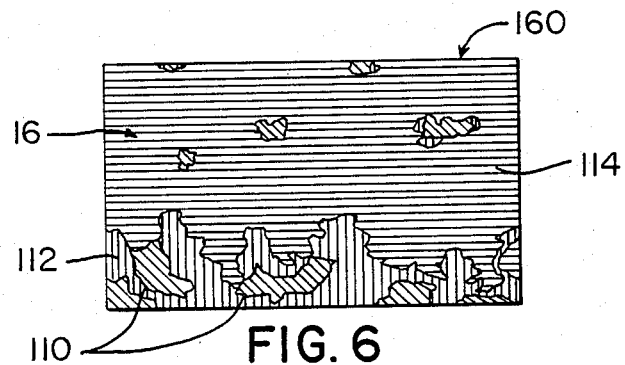
FIG. 6 is an example of a two-dimensional display of the chemical composition of the grain boundary in a plane therethrough being viewed from the aspect of arrow B shown in FIG. 4.

Then, after all data for the chemical composition and location of each sampled point in the microvolume are collected and stored in the computer storage 104, they are available for recall and analysis, for example, by display it with a printer 106 or on a video display, such as a CRT 108. FIGS. 5 and 6 illustrate examples of the manner in which such data can be recalled and displayed in beneficial formats for study and analysis of the grain boundary 16.

Figure 4:
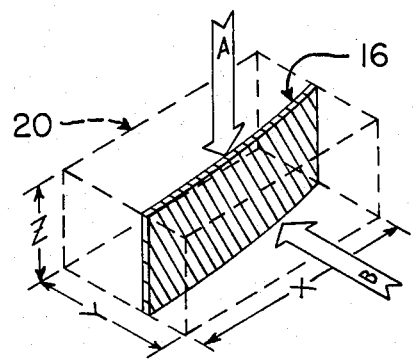
FIG. 4 is an enlarged isometric view of the microvolume analyzed according to this invention, including a portion of a grain boundary traversing therethrough.

The example display 150 selected for FIG. 5 is from a plan view aspect as indicated by arrow A in FIG. 4. It can be a plane at any chosen depth in the microvolume 20. When the aspect and position of the plane in the microvolume 20 are selected and specified by the appropriate X, Y, Z coordinates for that plane, the computer 100 will recall and display in correct spatial orientation the chemical composition data for each point sampled in that selected plane. For example, the plane selected for display in FIG. 5 is a transverse cross section of the grain boundary 16 at an arbitrary or desired depth. The zones or areas 110 displayed in green are those in which Si exceeds a selected level of concentration. The zones or areas 112 displayed in red are those in which SiO exceeds a selected level of concentration. The zones or areas 114 displayed in blue are those in which SiOH exceeds a selected level of concentration. Such threshold levels of concentration for display can be selected by the user, depending on what he or she wants to see for analysis. Also, although not shown here, the display can be set up to show different color shades or printer symbols for different levels of concentration of the chemical substances. For example, the computer 100 could be programmed to display areas of up to 10% concentration of SiOH in light blue, areas of 10% to 30% SiOH in medium blue, and areas of over 30% in dark blue, if the available plotter or printer has such capablities.

The display in FIG. 5 shows the effectiveness of hydrogen passivation in cross section in the three-dimensional grain boundary 16 at the level of the plane selected for display. The depth of penetration of the hydrogen passivation into the grain boundary 16 can be displayed by selecting a plane viewed from the aspect of arrow B in FIG. 4 that passes longitudinally through the three-dimensional grain boundary 16. Such a display 160 is illustrated in FIG. 6. It shows the hydrogen having penetrated to a substantial depth in the grain boundary 16 where the resulting SiOH zone or area 114 is displayed.

Any other area of interest can be viewed by simply selecting different planes through the microvolume 20 to be recalled and displayed by the computer 100 at desired levels of concentration. Such planes of view can be at any desired orientation and can also be curved, if desired, by selecting an appropriate curve definition for the X, Y, Z coordinate system as necessary to recall the desired points to be displayed.

While the foregoing description of this invention refers often to the analysis of grain boundaries in polycrystalline silicon, persons skilled in the art will also recognize the invention's applicability and utility for other analysis goals of the chemical compositions of solid devices. For example, the invention can be used to analyze depths of boron, arsenic, or phosphorous-doped junctions in semiconductor devices, as well as many other applications.

For purposes of example, and not for limitation, the SIMS 80 can be a "Cameca IMS-3f" (trademark) system. A "Hewelett-Packard 9845" (trademark) computer 100 with a "DEC" (trademark) dual hard disk can handle the control and data storage functions required by this invention. An "IDS Prism 135" (trademark) color printer can provide a good display of the data for analysis, or a standard high resolution video monitor can be used for such a display. Appropriate electronic digital control circuits and interconnections of these or other similar components to perform the desired functions can be used in a variety of ways that will be recognized and within the capabilities of persons having ordinary skill in the art, once the above description of the principles of this invention are read and understood.

The foregoing description is considered as illustrative only of the principles of the invention. Further, since numerous modifications and changes will readily occur to those skilled in the art, it is not desired to limit the invention to the exact construction and processes shown and described, and accordingly all suitable modifications and equivalents may be resorted to falling within the scope of the invention as defined by the claims that follow.

The embodiments of the invention in which exclusive property rights or privileges are claimed are defined as follows:

1. The method of determining and analyzing the chemical and compositional structure of solid devices, comprising the steps of:
    eroding a three-dimensional volume of the device in a predetermined erosion area and through a predetermined depth;
    during the eroding process, sampling and determining the types and concentrations of materials being eroded from individual ones of a plurality of points being simultaneously eroded from the surface area of the volume being eroded, and recording the types and concentrations of materials sampled at each such point along with the location of each such point in relation to the other points sampled in a manner that corresponds with their relative locations to each other in the three-dimensional volume; and
    displaying on a visual medium the types and concentrations of materials from the sampled points in any selected plane of analysis through the volume in such a manner that the types and concentrations of materials for each such point are displayed in relative locations to the types and concentrations of materials for the other points displayed corresponding to their relative locations in the three-dimensional volume.

2. The method of claim 1, including the steps of continuously rastering the sampling point by predetermined increments of space and time over the surface being eroded as the erosion process is being performed.

3. The method of claim 1, including the steps of eroding the volume by removing the material from the solid volume in separate molecular form and determining the types and concentrations of the materials by secondary ion mass spectrometry.

4. The method of claim 1, including the steps of eroding the volume by removing the material from the solid volume in separate molecular form and determining the types and concentrations of the materials by Auger electron spectroscopy.

5. The method of claim 1, including the steps of eroding the volume by removing the material from the solid volume in separate molecular form and determining the types and concentrations of the materials by x-ray photoelectron spectroscopy.

6. The method of claim 1, including the step of recording the location of each point in terms of positions on an X, Y, Z coordinate system where the X, Y, and Z components are perpendicular to each other.

7. The method of claim 6, including the steps of recording the location of each point along with the types and concentrations of materials at each point in a data base and displaying the types and concentrations of materials found in a selected plane of the volume in the format of a color-coded plot with separate colors representing each of the various types of material found in the selected plane.

8. The method of claim 7, including the step of selecting the plane of materials to be displayed in terms of the X, Y, Z coordinate system.

9. The method of claim 8, including the steps of selecting priority materials and threshold concentration levels for determining which of the material types is to be displayed for each point in the selected plane, and displaying the priority material that meets the selected threshold concentration level for each point in the selected plane.

10. Apparatus for determining and analyzing the chemical and compositional structure of solid devices, comprising:
    material removal means for gradually removing the material composition from a selected three-dimensional volume of the device;
    material determining means for determining the chemical types and concentrations of various materials removed from selected individual ones of a plurality of points being simultaneously removed the three-dimensional volume;
    recording means for recording the types and concentrations of the various materials removed from each of the selected points in conjunction with the location of each of such selected points in relation to the other selected points in a manner that corresponds with their relative locations to each other in the three-dimensional volume; and
    display means for displaying simultaneously the types and concentrations of the various materials removed from selected combinations of points in the volume in such a manner that the types and concentrations of materials for each such points are displayed in the relative locations to the types and concentrations of materials for the other points displayed corresponding to their relative locations in the three dimensional volume.

11. The apparatus of claim 10, wherein said material removing means includes sputtering means for eroding the material from the selected volume, and said material determining means includes a secondary ion mass spectrometer.

12. The apparatus of claim 11, wherein said secondary ion mass spectrometer includes collection means for collecting and routing into said secondary ion mass spectrometer the materials sputtered from a selected point on an exposed surface of said volume for secondary ion mass spectrometry determination of the chemical type and concentration of the materials sputtered from said selected point.

13. Apparatus for determining and analyzing the chemical and compositional structure of solid devices, comprising:

sputtering means for eroding the material composition from a selected volume of the device;

secondary ion mass spectrometer means for determining the chemical types and concentrations of various materials eroded from various selected points in the volume, said secondary ion mass spectrometer means including collection means positioned adjacent the eroding surface of the selected volume for collecting and routing into said secondary ion mass spectrometer means the materials sputtered from any selected point on an exposed surface of said volume for determination by secondary ion mass spectrometry of the chemical type and concentration of the materials sputtered from the selected point;

raster means connected to said collection means for selecting sequential points of collection by rastering the collection means in selected increments of space and time over the exposed surface of the volume simultaneously with operation of the sputtering means;

recording means for recording the types and concentrations of the various materials removed from the selected points in conjunction with the location of each of such points; and display means for displaying simultaneously the types and concentrations of the various materials removed from selected combinations of points in the volume.

14. The apparatus of claim 13, wherein said raster means includes adjustable electrostatic lens means for focusing said collection means to collect a sample from a selected point, and automatic drive means for adjusting said electrostatic lens means to focus said collection means on selected different points.

15. The apparatus of claim 14, wherein said electrostatic lens means includes an electric field to focus the collection means on a selected point and is adjustable along perpendicular X-Y coordinates on the surface of the volume by varying the voltages applied to opposite sides of the electric field, and said automatic drive means includes digital computer means for selecting and causing variations in the voltages applied to the electric field to raster the collection means in the selected increments of space and time.

16. The apparatus of claim 10, wherein said display means includes plotter means for plotting in relative spacial positions the various types and concentrations of materials sputtered from the respective points in a selected plane.

17. The apparatus of claim 16, wherein said display means displays the respective various types of materials in the form of unique symbols for each of said materials.

18. The apparatus of claim 17, wherein said unique symbols are individual colors for each of said materials.

19. The apparatus of claim 13, including computer means connected to said material determining means and to said raster means and to said display means for recording the types and concentrations of materials and the respective point locations in a data base and for controlling said raster means and for recalling the types and concentrations of materials in a selected plane and for causing the display means to display the types and concentrations of materials in the selected plane.

* * * * *